United States Patent
Konstantinova et al.

(10) Patent No.: US 6,476,036 B1
(45) Date of Patent: Nov. 5, 2002

(54) SODIUM SALT OF 3-(4-CINNAMYL-1-PIPERAZINYL)-IMINO-METHYL RIFAMYCIN SV

(76) Inventors: Roumiana Gueorguieva Konstantinova, Stara planina Strasse 17, 1504 Sofia (BG); Kiril Asenov Ninov, Soultan tepe Str. 18, 1505 Sofia (BG); Velitchka Ilieva Dimova, Mladoct 1, B1.66A, Vh.B, 1784 Sofia (BG); Anka Veltcheva Evstatieva, Hadji Dimitar B1.27A, 1510 Sofia (BG)

( * ) Notice: Subject to any disclaimer, the term of this patent is extended or adjusted under 35 U.S.C. 154(b) by 0 days.

(21) Appl. No.: 09/831,012
(22) PCT Filed: Nov. 3, 1999
(86) PCT No.: PCT/BG99/00022
§ 371 (c)(1),
(2), (4) Date: May 3, 2001
(87) PCT Pub. No.: WO00/25721
PCT Pub. Date: May 11, 2000

(30) Foreign Application Priority Data

Nov. 4, 1998 (BG) ................................................ 102897

(51) Int. Cl.$^7$ ..................... A61K 31/496; C07D 405/06
(52) U.S. Cl. .................................. 514/254.11; 540/458
(58) Field of Search ....................... 540/458; 514/254.11

(56) References Cited

U.S. PATENT DOCUMENTS 4,193,920 A * 3/1980 Konstantinova et al. ........................................................... 514/254.11
4,918,066 A     4/1990 Kump ........................ 514/183

FOREIGN PATENT DOCUMENTS

GB       2200353 A    *  8/1988

* cited by examiner

*Primary Examiner*—John M. Ford
(74) *Attorney, Agent, or Firm*—Webb Ziesenheim Logsdon Orkin & Hanson, P.C.

(57) ABSTRACT

Sodium salt of 3-(4-cinnamyl-1-piperazinyl)-iminomethyl rifamycin SV was synthesized. The compound shows high activity against Gram-positive and Gram-negative microorganims, Mycobacterium tuberculosis (including atypical and rifampicin resistant) and may be used in the medical practice. The sodium salt has formula (II). The process for preparation of the sodium salt consists of reacting equimolar quantities of 3-(4-cinnamyl-1-piperazinyl)-iminomethyl rifamycin SV and sodium ascorbate with addition of 30% methanol solution of sodium methylate, followed by filtration and removement of the solvent by distillation under reduced pressure. The compound can also be obtained from the sodium salt of 3-formil rifamycin SV, which is reacting with $N^1$-amino-$N^4$-cinnamypiperazin in medium of inert solvent at room temperature.

3 Claims, No Drawings

SODIUM SALT OF 3-(4-CINNAMYL-1-PIPERAZINYL)-IMINO-METHYL RIFAMYCIN SV

Sodium salt of 3-(4-cinnamyl-1-piperazinyl)-iminomethyl rifamycin SV was synthesized.

The compound shows high activity against Gram-positive and Gram-negative microorganisms, Mycobacterium tuberculosis (including atypical and rifampicin resistant) and may be used in the medical practice. The sodium salt has the following formula:

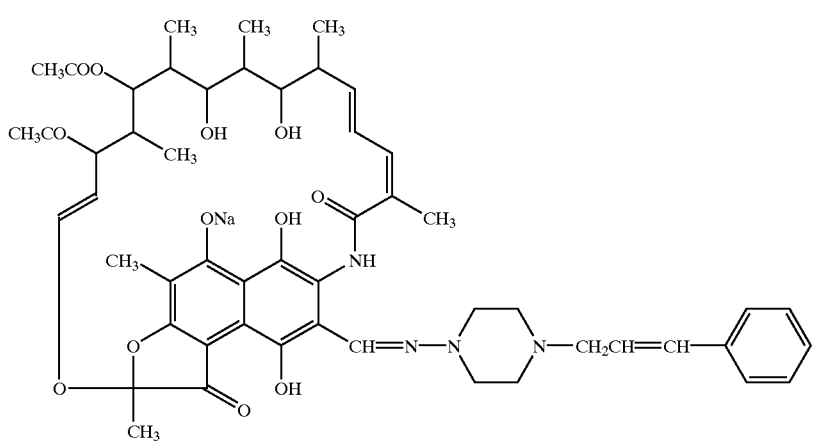

Formula II

The process for preparation of the sodium salt consists of reacting equimolar quantities of 3-(4-cinnamyl-1-piperazinyl)-iminomethyl rifamycin SV and sodium ascorbate with addition of 30% methanol solution of sodium methylate, followed by filtration and removement of the solvent by distillation under reduced pressure.

The compound can also be obtained from the sodium salt of 3-formil rifamycin SV, which is reacting with $N^1$-amino-$N^4$-cinnamypiperazine in medium of inert solvent at room temperature.

TECHNICAL FIELD

The invention relates to the sodium salt of 3-(4-cinnamyl-1-piperazinyl)-iminomethyl-rifamycin SV and process of preparation. The sodium salt shows high activity against Gram-positive and Gram-negative microorganisms, Mycobacterium tuberculosis, (including atypical and Rifampicin resistant) and therefore may be used in the medical practice.

BACKGROUND OF THE INVENTION

The rifamycins are group of antibiotics with high antibacterial activity and they have a wide spectrum of application in the treatment of Mycobacterium infections. Rifampicin is the best known representative of the group of rifamycins.

In document BG No. 36006 (U.S. Pat. No. 4,193,920) are described new azomethyn derivatives of Rifamycin SV with general formula I,

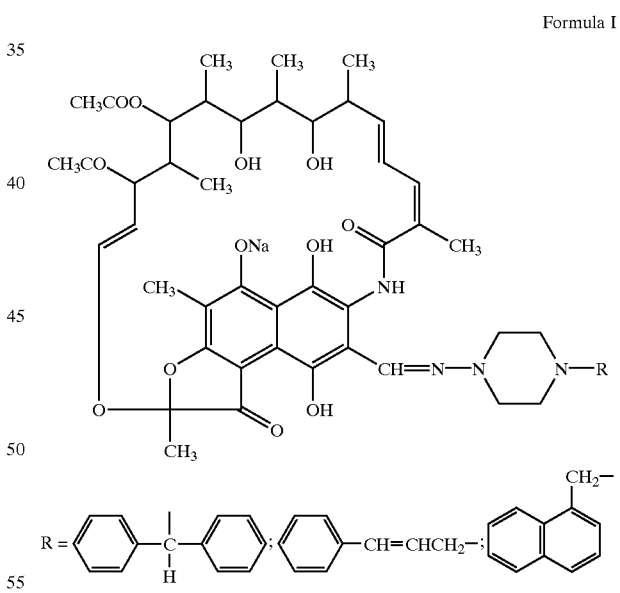

Formula I

These compounds display high activity against Gram-positive and Gram-negative microorganisms and Mycobacterium tbc. This activity is analogical and in some cases is higher than that of Rifamycin. The document BG No. 87451 (U.S. Pat. No. 5,095,108 (1992)) describes a process for preparing the insoluble crystal form of 3-(4-cinnamyl-1-piperazinyl)-iminomethyl rifamycin SV (compound, designed as T-9 in the first quoted BG document). The in vivo investigations of the compound show a higher therapeutic effect in comparison with this of Rifampicin. The therapeutic activity of T-9 in doses 10 mg/kg in generalized tuberculosis in test animals shows full organ sterilization after 60 days of treatment, while a similar therapeutic effect is achieved with Rifamificyn in doses of 80 mg/kg. The compound presents considerably longer serum half life than Rifampicin ($T_{1/2}$: 31~34 hours) tested on animals.

The acute toxicity of T-9 in mice is 4000 mg/kg, while this of Rifampicin is 1500 mg/kg. This indicates the compound T-9 as the best perspective among the derivatives of Rifamicyn SV, described in BG No. 36006.

DISCLOSURE

The present invention is concerned with the sodium salt of 3-(4-cinnamyl-1-piperazinyl)-iminomethyl rifamycin SV which is new, and a process for its preparation. The new sodium salt provided by the present invention is compound of the general formula II:

| Method of Application Species of Animals | | | $C_{max}$ mg/ml | $T_{max}$ h | $T_{1/2}$ h | AUC mg · h/ml | CL ml · min/kg | V J/kg |
|---|---|---|---|---|---|---|---|---|
| Mice | T-11 | i.v | 50 | 1 | 39.08 | 3616.7 | 0.092 | 0.312 |
| | | p.o | 14.4 | 8 | 38.02 | 977.45 | 0.092 | 0.303 |
| | T-9 | p.o | 12.4 | 8 | 33.70 | 734.69 | 0.092 | 0.270 |
| Rats | T-11 | p.o | 9.20 | 2 | 20.04 | 671.352 | | |
| | T-9 | p.o | 8.20 | 6 | 21.18 | 543.144 | | |
| Rabbits | T-11 | p.o | 2.71 | 2 | 28.04 | 298.8 | | |
| | T-9 | p.o | 2.75 | 2 | 56.63 | 232.6 | | |

The advantages of the newly-synthesed sodium salt are the good water solubility and the possibility of its application in the form of injection solutions (which is impossible with the unsoluble starting compound T-9), good stability of the obtained water solutions, faster resorbtion and better pharmacokinetic properties in animal tests.

Formula II

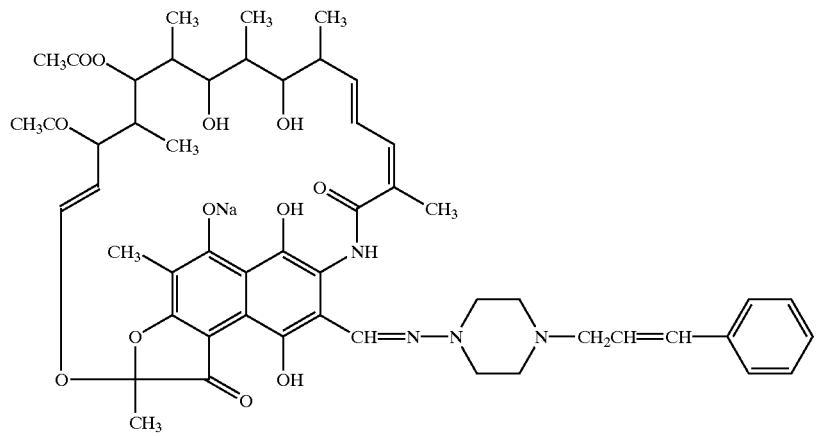

The new sodium salt of 3-(4-cinnamyl-1-piperazinyl)-iminomethyl rifamycin SV has increased antibacterial activity and low toxicity in comparison with the compound "T-9". The new sodium salt has the following advantages: good water solubility and higher bioavalability and possibility for administration as injectable formulation.

The synthesis of the water soluble sodium salt of "T-9" provides better possibilities for administration of the new salt as well in parenteral as in peroral pharmaceutical formulations.

The in vitro studies of the activity of sodium salt (designated T-1 1) in comparison with the initial compound T-9 show good antibacterial activity against the Gram-positive microorganisms including aerobic, anaerobic and Mycobacterium (typical and atypical). The pharmacokinetic properties of the known compound T-9 are improved in the salt—the sodium salt has better resorbtion characteristics resulting from its better water solubility and it maintains higher serum levels. The sodium salt has clearly expressed depo activity and secures the maintenance of constant theurapeutical concentrations in the organism for a longer period of time: 40~50 hours in mice and rats, and about 100 hours in rabbits (Table 1).

TABLE 1

Non-model pharmacokinetic parameters after use of T-11 and T-9 (base 20 mg/kg) in mice, rats and rabbits The sodium salt of 3-(4-cinnamyl-1-piperazinyl)-iminomethyl rifamycin SV can be easily obtained by the following two methods:

Method A.

In this method the sodium salt of 3-(4-cinnamyl-1-piperazinyl)-iminomethyl rifamycin SV is prepared by reacting equimolar amount of 3-(4-cinnamyl-1-piperazinyl)-iminomethyl rifamycin SV and of appropriate organic or inorganic base, containing sodium, in aqueous medium or in organic solvent medium. Preferably the reaction can be carried out in the presence of small amount of sodium ascorbate as an antioxidizing agent to prevent the transformation of the phenol structures in the rifamycin derivative into quinine-structures. When the reaction is carried out in an aqueous medium, diluted solution of sodium salt is used as a base and when using sodium alcoholates (sodium methylate, sodium ethylate, sodium isopropilate), the reaction mixture is prepared by adding the corresponding alcohol (methanol, ethanol and the like). More preferably is the use of sodium methylate diluted with methanol or ethanol. The solvent was removed in vacuum (if it is alcoholate) and the resulting solid sodium salt is distillated or is lyophilized (if the reaction is carried out in aqueous medium).

The sodium salt may be isolated using distillation of the solving agent in vacuum (when effecting the reaction in an alcoholic medium), or using lyophilization (when effecting the reaction in water).

The yield of the sodium salt is practically quantitative and with high purity. The obtained sodium salt may be purified by recrystallization in a suitable solvent.

Method B.

Proceeding as described in Method A is prepared a sodium salt of 3-formil rifamycin SV which subsequently is reacting with $N^1$-amino-$N^4$-cinnamylpiperazine in medium of an inert solvent at room temperature. The solvent was evaporated by distillation in vacuum and the residual product was purified by recrystallization in suitable solvent.

The following examples are given to illustrate more clearly the present invention.

EXAMPLE 1

4,62 g (0,005 g/moll) of 3-(4-cinnamyl-1-piperazinyl)-iminomethyl rifamycin SV is suspended in 40 ml methanol and 0,1 g sodium ascorbate dissolved in 1 ml water is added. To the obtained suspension 0,9 ml of 30% methanol solution of sodium methylate (equimolar quantity) is added. The suspension immediately turns into a solution because of the formation of the sodium salt. The reaction mixture is filtered to remove the unsolved sediment of sodium ascorbate, and the solvent is concentratrated in vacuum and dried to give the soduim salt as a dark-red solid powder. This product has high purity and the yield is practically quantitative. The crude product opptionally may be recrystallized by boiling in isopropanol to give the sodium salt as red crystal solid (80% yield), soluble in water, methanol, ethanol, acetone and unsoluble in isopropanol.

The absorption in UV-spectrum and visible area of 0,001% methanol solution of the product in the interval 200–800 nm in cuvette, with layer with 1 cm, has a maximums wavelength of 251, 338 and 480 nm.

Analysis: $C_{51}H_{63}N_4 NaO_{12}$ M.m 947,03

% content of Na (theoretical): 2,43

% content of Na (determined by the method of atomic-absorption analysis): 2,35

EXAMPLE 2

In a manner analogous to that described in Example 1 and substituting the methanol with ethanol the sodium salt was obtained.

EXAMPLE 3

In a manner analogous to that described in Example 1 and substituting the methanol with isopropanol the sodium salt was obtained.

EXAMPLE 4

In a manner analogous to that described in Example 1 and subsituting the 30% methanol solution of sodium methylate with equimolar quantity of dry sodium methylate the sodium salt was obtained.

EXAMPLE 5

4,62 g (0,005 g/moll) of 3-(4-cinnamyl-1-piperazinyl)-iminomethyl rifamycin SV is suspended in 100 ml of water, and 5 ml 1N solution of sodium base is added to the suspension for two to three hours with vigirous stirring. A gradual transformation of the suspension into a solution is observed, due to the formation of the soluble sodium salt. The reaction mixture is filtered and lyophilized to give the sodium salt as dark red powder (quantitative yield).

Analysis: $C_{38}H_{46}NNaO_{13}$

% content of Na (theoretical): 3,07

% content of Na (determined by the method of atomicabsorbation analysis): 3,05

EXAMPLE 6

5,23 g (0,007 g/moll) of the obtained product is dissolved in 50 ml tetrahydrofuran and to the solution with continuous stirring 1,52 g (0,007 g/moll) $N^1$-amino-$N^4$-cinnamylpiperazine, dissolved in 20 ml tetrahydrofuran, is added. The reaction mixture is stirred at room temperature for 2 h. The solvent is then redistillated under reduced pressure. The obtained sodium salt of 3-(4-cinnamyl-1-piperazinyl)-iminomethyl rifamycin SV is recrystallized in isopropyl alcohol. Yield of 4,97 g (75%)

The product is identical to this obtained by the procedure in Example 1.

What is claimed is:

1. Sodium salt of 3-(4-cinnamyl-1-piperazinyl)-iminomethyl rifamycin SV of the formula:

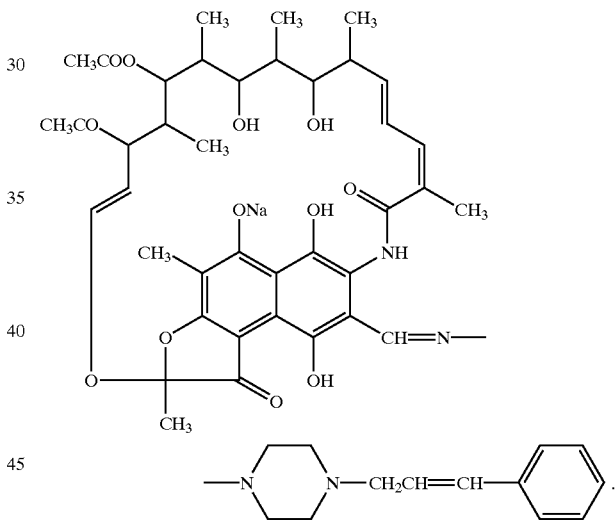

2. A method for the treatment of diseases caused by bacterial infections comprising administering an effective amount of a sodium salt of 3-(4-cinnamyl-1-piperazinyl)-imino-methyl rifamycin SV.

3. A pharmaceutical formulation for the treatment of diseases caused by bacterial infections comprising a unit dose of a sodium salt of 3-(4-cinnamyl-1-piperazinyl)-imino-methyl rifamycin SV and a pharmaceutical excipient.

* * * * *

UNITED STATES PATENT AND TRADEMARK OFFICE
CERTIFICATE OF CORRECTION

PATENT NO. : 6,476,036 B1  Page 1 of 1
DATED : November 5, 2002
INVENTOR(S) : Roumiana G. Konstantinova et al.

It is certified that error appears in the above-identified patent and that said Letters Patent is hereby corrected as shown below:

<u>Title page,</u>
Item [86], § 371 date, "May 3, 2001" should read -- July 20, 2001 --.

Item [76], Inventors, address of third inventor, Dimova, "Mladoct" should read -- Mladost --.

<u>Column 1,</u>
After the Title and before TECHNICAL FIELD, delete text and Formula II.

<u>Column 2,</u>
Formula I, "ONa" in center of Formula I should read as follows -- OH --.

Signed and Sealed this

First Day of July, 2003

JAMES E. ROGAN
*Director of the United States Patent and Trademark Office*